United States Patent

Labarre et al.

[11] 4,317,773
[45] Mar. 2, 1982

[54] INORGANOCYCLIC COMPOUNDS USABLE AS MEDICAMENTS AND A PROCESS FOR THEIR PREPARATION

[75] Inventors: Jean-François Labarre; François Sournies, both of Toulouse, France; Johan C. van de Grampel, Paterswolde; Andriaan A. van der Huizen, Groningen, both of Netherlands

[73] Assignee: Agence Nationale de Valorisation de la Recherche (ANVAR), France

[21] Appl. No.: 162,759

[22] Filed: Jun. 25, 1980

[30] Foreign Application Priority Data

Jul. 4, 1979 [FR] France ................................ 79 17336

[51] Int. Cl.³ ........................ C07F 9/56; A61K 31/675
[52] U.S. Cl. .............................. 260/239 EP; 424/200; 546/22; 544/232; 544/243; 544/337; 260/326.61; 548/111
[58] Field of Search ................... 424/244; 260/239 EP

[56] References Cited

PUBLICATIONS

Faucher et al. J. Chem. Res. (M) 1977, 1255.

*Primary Examiner*—Mark L. Berch

*Attorney, Agent, or Firm*—Maky, Renner, Otto & Boisselle

[57] ABSTRACT

The invention relates to new chemical compounds corresponding to the followings formula

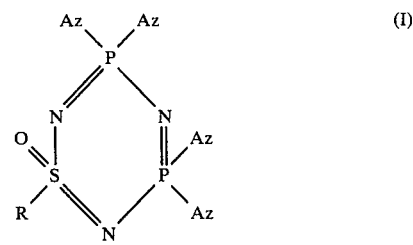

in which R is a non-hydrolyzable radical and Az represents aziridinyl

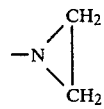

These compounds may be used as medicaments.

6 Claims, 1 Drawing Figure

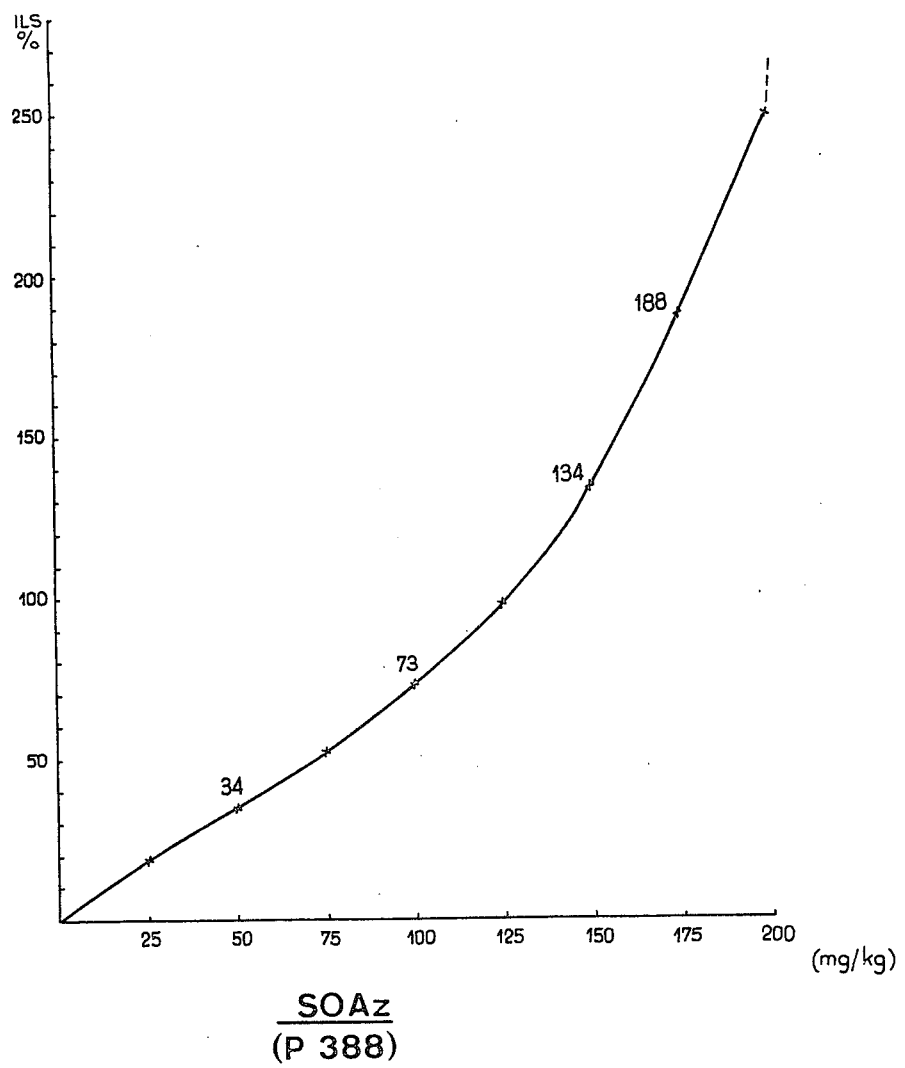

INORGANOCYCLIC COMPOUNDS USABLE AS MEDICAMENTS AND A PROCESS FOR THEIR PREPARATION

This invention relates to new compounds suitable for use as medicaments, particularly in the treatment of tumours.

The compounds according to the invention are related to the non-carbon-containing heterocyclic derivatives of the cyclophosphazene type of which a certain number have already been described in the literature.

The prior-art compounds include compounds corresponding to the following formula:

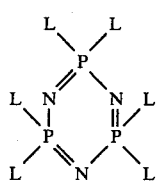

in which: L represents a chlorine atom, a pyrrolyl or aziridinyl radical, which are described in the Article by J. F. LABARRE et al in Europ. J. Cancer, Vol. 15, pp 637–643, 1979.

These compounds and, in particular, the derivative in which L is an aziridinyl radical show interesting antitumoral activity.

The research work carried out by the inventors has resulted in the discovery of new heterocyclic derivatives of the cyclophosphathiazene type of which the basic ring is the following:

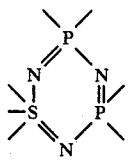

and of their remarkable antitumoral properties.

Certain compounds derived from the cyclophosphathiazene structure were already known from the prior art, particularly from the works of one of the inventors which are recalled in the course of the present description. However, these Articles do not suggest the possibility of obtaining antitumoral compounds from the compounds described in these Articles.

The cyclophosphathiazene-type structure has the chemical advantage, particularly over the cyclophosphazene derivatives, of possessing a sulphur atom which preferably carries an oxygen atom and of which the free bond may be attached to a large number of radicals. This possibility of varying the nature of the substituent of the sulphur atom opens the way to a very large family of active compounds containing this substituent of the sulphur atom as the "activity modulator" element.

More particularly, the present invention relates to compounds corresponding to the following formula:

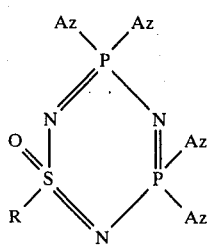

in which R is a radical which cannot be hydrolysed at room temperature and at a neutral pH-value and Az is a substituted or unsubstituted 1-aziridinyl radical.

Particularly interesting compounds of formula I include compounds corresponding to the following formula

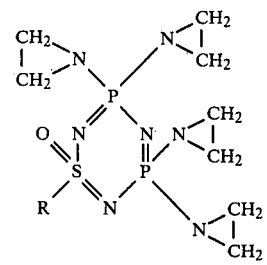

in which R is as defined above.

Preferably, the radical R is:
a halogen atom,
an unsubstituted or substituted alkyl radical,
an unsubstituted or substituted alkenyl radical,
an unsubstituted or substituted alkynyl radical,
an unsubstituted or substituted aryl radical,
an unsubstituted or substituted alkoxy radical,
an unsubstituted or substituted aryloxy radical,
a hydroxy radical, an amino radical,
an N-substituted or N,N-disubstituted amino radical.

Suitable substituents of the 1-aziridinyl radical Az are in particular the alkyl and alkoxy radicals.

In the context of the invention, the term "alkyl radical" used in particular in the definition of R and for the substituents of the radical Az is understood to apply in particular to lower straight-chain or branched alkyl radicals containing in particular from 1 to 7 carbon atoms, such as the methyl, ethyl, n-propyl, n-butyl, isobutyl, t-butyl, pentyl and hexyl radicals.

The term "alkenyl radical" is understood to apply in particular to lower straight-chain or branched alkenyl radicals containing in particular from 2 to 7 carbon atoms and comprising one or several ethylenic unsaturations, such as the vinyl, alkyl, butadienyl radicals for example.

The term "alkynyl radical" is understood to apply in particular to lower straight-chain or branched alkynyl radicals containing in particular from 2 to 7 carbon atoms, such as the acetynyl and propargyl radicals.

The alkyl, alkenyl or alkynyl radicals according to the present invention may be unsubstituted or substituted, in particular by halogen atoms, for example in the trifluoromethyl radicals, or by an aryl radical, as for example in the benzyl radical.

The N-substituted amino radicals include in particular N-alkyl radicals in which the alkyl radicals are as defined above, for example N-methylamino, N- ethylamino, N-propylamino and N-hexylamino radicals.

The N,N-disubstituted amino radicals include in particular N,N-dialkyl radicals in which the alkyl radicals are as defined above, for example the N,N-dimethylamino, N,N-diethylamino and N-methyl-N-ethyl amino radicals.

The substituents of the N-substituted and N,N-disubstituted radicals may be different from the alkyl radicals and may be in particular $C_3$–$C_6$-cycloalkyl radicals, for example the N-cyclohexylamino and N,N-dicyclohexylamino radicals.

The substituents of the amino radical may also form a ring with the nitrogen atom, as for example in the aziridinyl pyrrolyl, imidazolyl, pyrazolyl, pyridyl, pyrimidinyl, pyrazinyl, pyrrolidinyl, imidazolidinyl, piperidyl and piperazinyl radical. This ring may obviously be aromatic or non-aromatic and may contain hetero atoms other than the nitrogen atom, for example the isoxazolyl, furazannyl and morpholinyl radicals; this ring may also be substituted, in particular by one or more alkyl or alkoxy radicals.

The term "alkoxy radical" used in particular in the definition of R and for the substituents of the radical Az is understood to apply essentially to the $C_1$–$C_7$-alkoxy radicals corresponding to the alkyl radicals mentioned above, for example methoxy, ethoxy and butoxy, and optionally containing substituent of the same type.

The term "aryl radical" is understood to apply essentially to monocyclic radicals, particularly the phenyl radical, the aryl radical, capable of substitution in different ways, particularly by one or more of the alkyl radicals defined above, alkoxy radicals defined above, or halogen such as tolyl, xylyl, ethyl-phenyl, propyl-phenyl, diethyl-phenyl, bromophenyl, chlorophenyl and dichlorophenyl for example.

The term "aryloxy" radical is understood to apply essentially to the aryloxy radicals corresponding to the aryl radical mentioned above which may optionally carry the same substituents as in the case of the aryl radical.

Particularly preferred compounds according to the present invention include those compounds in which the radical R is a phenyl, aziridinyl radical or a fluorine atom.

The present invention also relates to a process for the preparation of the above-defined compounds in which the optionally substituted aziridine Az—H is reacted with a compound corresponding to the formula

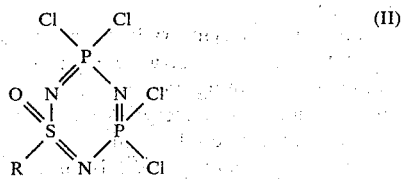

in which R is as defined above.

This reaction is preferably carried out in a dry solvent, in particular:

an ether, such as dimethyl ether, diethyl ether and tetrahydrofuran, an aliphatic hydrocarbon, such as hexane and heptane, an aromatic solvent, such as benzene, toluene and nitrobenzene, or a nitrile, such as acetonitrile.

The reaction is carried out at a temperature of from +100° C. to −100° C., preferably at a temperature of from +60° C. to −90° C. and, more particularly, at a temperature of the order of −75° C.

The above reaction may be carried out in the presence of an HCl acceptor other than the aziridine itself, for example a tertiary amine, an alkali hydroxide, an alkali carbonate, an alkali-earth hydroxide or an alkali hydrogen carbonate.

The molar ratio of the compounds to be reacted is not a critical parameter although, in view of the fact that the aziridine also acts as hydrochloric acid acceptor, it is preferred to use an excess of optionally substituted aziridine in relation to the stoeichiometric quantity.

The reaction product corresponding to formula I may be purified by known processes, such as solvent extraction, crystallisation, liquid phase chromatography, high-performance liquid phase chromatography ("HPLC") for example.

Where the radical R is an amino, N-substituted amino or N,N-disubstituted amino radical or an alkoxy or aryloxy radical, the corresponding compound of formula I may be prepared by reaction of a compound corresponding to the formula

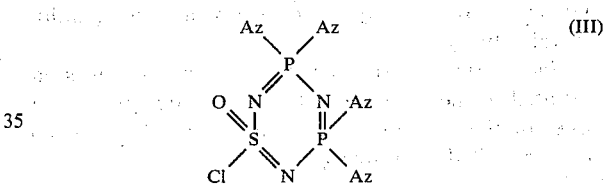

with the amine respectively the hydroxy derivative corresponding to the desired radical R.

The reaction is carried out preferably at low temperature, for example under 20° C.

Where the radical R is the hydroxy radical, the corresponding compound of formula I may be prepared by hydrolysis of the corresponding compound of formula III at a temperature above 50° C.

The reaction of compound III with amine, hydroxy derivatives or water is preferably carried out in the presence of an HCl acceptor such as those mentioned above.

When the reactant is an amine, an excess of this amine may be used as HCl acceptor.

Because the compound of formula III is difficult to isolate it may be prepared and used in situ if necessary from a compound corresponding to the following formula

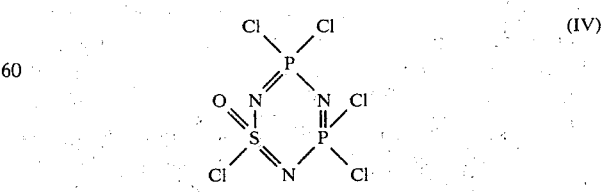

by the action of aziridine.

The reaction of compound IV with aziridine may be carried out in the presence of an HCl acceptor especially an excess of aziridine of about 8 moles of aziridine for each mole of compound IV.

Compounds of formula I in which R=Az may be directly obtained from the compound of formula IV by the action of excess aziridine under conditions identical with those mentioned for the reaction of the compound of formula II with aziridine. The excess of aziridine used in this process is preferably a great excess, for example more than 10 moles of aziridine for 1 mole of compound IV to 30 moles of aziridine for 1 mole of compound IV.

The compound of formula IV is a known compound or may be prepared as described in:

H. H. BAALMANN, H. P. VELVIS, J. C. van de GRAMPEL, Rec. Trav. Chim. (Netherlands) 91, 935-941 (1972).

The various starting compounds suitable for use in the process according to the invention may be prepared in particular in the processes described in:

H. H. BAALMANN and J. C. van de GRAMPEL, Rec. Trav. Chim. (Netherlands) 92, 1237-1239 (1973), H. H. BAALMANN, H. P. VELVIS, J. C. van de GRAMPEL, Rec. Trav. Chim. (Netherlands) 91, 935-941 (1972), J. B. van den BERG, B. de RUITER, J. C. van de GRAMPEL, Z. Naturforsch. 31b, 1216-1218 (1976).

EXAMPLE OF PREPARATION OF THE STARTING COMPOUND $(NPCl_2)_2NSOF$

A mixture of 1.3 g (3.9 mM) of $(NPCl_2)_2NSOCl$ and 6.5 g (44.6 mM) of $AgF_2$ in 15 ml of dry carbon tetrachloride is stirred in darkness for 20 hours at room temperature. The solvent phase is then filtered free from solids and evaporated under reduced pressure to dryness.

Sublimation at 40° C. under a pressure of 0.1 mm Hg gives 0.75 g (2.4 mM) of $(NPCl_2)_2NSOF$ in a pure form melting at 37° to 38° C. (uncorrected), corresponding to a yield of 61%.

Elemental analysis: Calculated: N 13.43; S 10.25; F 6.07; Cl 45.33. Observed: N 13.31; S 10.18; F 5.9; Cl 45.67; N 13.27; S 10.07; F 6.0; Cl 45.54.

IR ($cm^{-1}$) in the region 400-1400 $cm^{-1}$ (nujol) 498w, 522m, 541vs, 615vs, 672m, 711s, 810s, 8778m, 1114w, 1198vs, 1223vs, 1364vs.

EXAMPLE OF PREPARATION OF THE STARTING COMPOUND $(NPCL_2)_2NSOPh$

A mixture of 2.6 g (7.8 mM) of $(NPCl_2)_2NOCl$ and 1.05 g (7.8 mM) of aluminum chloride in 80 ml of benzene is heated under reflux with stirring for 48 hours and then cooled to ambient temperature and subsequently poured into a mixture of concentrated hydrochloric acid and crushed ice (ratio by volume 1:7). The aqueous phase is extracted twice with 25 ml of benzene and the benzene phases are combined and washed with water, dried over $CaCl_2$ and evaporated to dryness under reduced pressure.

The product is purified by recrystallisation from n-pentane. $(NPCl_2)_2NSOPh$ is thus obtained in a yield of 4.9 g, corresponding to 85%.

Elemental analysis: Calculated: C 19.43; H 1.36; P 16.70; S 8.64; Cl 38.23. Observed: C 19.43; H 1.38; P 16.35; S 8.70; Cl 38.07; C 19.33; H 1.36; P 16.54; S 8.79; Cl 38.13.

IR ($cm^{-1}$) 470m, 535s, 555s, 602s, 615sh, 670m, 685m, 695m, 755s, 770m, 835s, 870m, 1000w, 1024w, 1100s, 1187vs br, 1240sh, 1272s.

Finally, the present invention concerns, as a new medicament and in particular as an antitumoral agent, a compound of the type described above and pharmaceutical compositions containing as active principle at least one of these compounds and, more particularly, pharmaceutical compositions designed for parenteral administration.

The compositions designed for parenteral administration include injectable compositions, particularly intraperitoneally and intravenously injectable compositions, although other compositions, such as pellets, may be used. Since the products in question are fairly soluble in water, an aqueous solvent, for example a physiological sodium chloride solution, will preferably be used as pharmaceutical support. In the case of sparingly soluble products, it is of course possible to use buffers which modify the pH or possibly a non-aqueous solvent, such as esters, alcohols, polyols or various oils, in combination with emulsifiers. It is also possible to use suspensions, particularly of hydroxypropyl celluloses.

Although the pharmaceutical compositions according to the present invention are preferably injectable compositions, it is also possible to use compositions designed for digestive, sublingual, oral or rectal administration which may be made up in solid forms as tablets, cachets, granules, capsules, suppositories for example, or in liquid form as drops and ampoules.

Compositions designed for oral administration are formulated with known solid supports, such as gelatin, gum arabic, lactose, starch, polyalkylene glycol, carboxymethyl cellulose for example.

In the case of suppositories, it is possible to use polyethylene glycol and lanolin as vehicle.

The compositions according to the present invention may also be topically administered, in particular in the form of an ointment or gel applicable to the skin with an inert vehicle, such as vaseline, polyethylene glycol or other fatty excipients; it is also possible to use an agent which facilitates the cutaneous penetration of the active principle.

Generally, the compositions according to the present invention may contain various adjuvants, such as preservatives, stabilisers, wetting agents, emulsifiers, texturisers, disintegrating agents, flavourings, colorants.

The compounds according to the present invention may be used for the treatment of liquid or solid tumours, for example leukaemias, melanomas, sarcomas, carcinomas. Some of the compounds according to the invention have proved to be particularly active in the treatment of leukaemias, as demonstrated by the following examples of activity on leukaemia P 388.

The present invention also relates to a process for the treatment of solid or liquid tumours which comprises administering to a patient suffering from such a tumour an effective quantity of at least one compound corresponding to general formula I and in particular of a compound corresponding to general formula I'.

The doses administered are of course dependent in each case on the type of tumour to be treated and on the general state of the patient to be treated and may vary within wide limits, but are generally in the range from 0,2 to 300 mg/kg per day and particularly in the range from 10 to 300 mg/kg per day for the injectable forms, oral forms, suppository form and ointment forms, in one or several times of which the frequency may be variable according to the respective toxicity of each of the products.

Thus, the single doses for the injectable forms and for oral administration are preferably from 5 to 500 mg and more particularly from 10 to 400 mg of active principle.

In the case of suppositories, the single doses are from 10 to 1000 mg and preferably from 50 to 1000 mg. So far as ointments are concerned, concentrations of from 1 to 20% by weight are preferred.

The following Examples are intended to illustrate the method of preparation of some of the compounds according to the invention without limiting the invention in any way.

EXAMPLE 1

Preparation of the compound (NPAz$_2$)$_2$NSOF

A solution of 48.0 mMoles of freshly distilled aziridine in 40 ml of dry diethylether is added dropwise over a period of 1 hour to a solution of 3.0 mMoles of (NPCl$_2$)$_2$NSOF in 40 ml of dry diethylether cooled to a temperature of $-75°$ C. (mixture of acetone and liquid nitrogen) under vigorous stirring. The reaction mixture is left to return slowly to room temperature, followed by stirring for another 17 hours at that temperature.

The solution is decanted and the residue (consisting largely of polymeric material) is extracted three times with portions of 20 ml of dry diethylether.

After the mother liquor and the extracts have been combined, the solvent is evaporated in vacuo. The crude reaction product is extracted with three portions of 80 ml of dry diethylether.

Recrystallisation by partial evaporation of the solvent and subsequent cooling of the solution gives a crystalline material having a melting point of 111°–112° C. in a yield of 62%.

The compound has the following analytical characteristics:

Analysis: Calculated: C 28.32; H 4.75; N 28.90; S 9.45. Observed: C 28.20; H 4.70; N 28.75; S 9.49; C 28.16; H 4.72; N 28.68; S 9.68.

IR (cm$^{-1}$) in the region 400–1400 cm$^{-1}$ (nujol) 1320s, 1273vs, 1234vs, 1167sh, 1153s, 1122m, 1096m, (960, 942)vs, 881m, 848m, 811m, 708s, 669s, 650vs, 525m.

Mass spectrum m/e 339 (M+) 13%, 297 (M-Az)+ 100%.

$^{31}$p NMR (in solution in CDCl$_3$) $\delta^{31}$p 35.7 ppm (in relation to 85% H$_3$PO$_4$) J(P-F) 3.7 Hz.

By using monomethylaziridine in state of aziridine the compound (NP(AzCH$_3$)$_2$)$_2$NSOF is obtained.

EXAMPLE 2

Preparation of the compound (NPAz$_2$)$_2$NSOAz

A solution of 90.0 mMoles of freshly distilled aziridine in 40 ml of anhydrous ether is added dropwise over a period of 1 hour to a solution of 4.5 mMoles of (NPCl$_2$)$_2$NSOCl in 40 ml of dry diethylether cooled to $-75°$ C. (mixture of acetone and liquid nitrogen) under vigorous stirring. The reaction mixture is left to return slowly to room temperature, followed by stirring for another 17 hours at that temperature. The solution is filtered and the residue (consisting essentially of polymeric material) is extracted three times with 30 ml of dry diethylether.

After the mother liquor and the extracts have been combined, the solvent is evaporated in vacuo. The crude reaction product is extracted with three portions of 80 ml of diethylether.

Recrystallisation by partial evaporation of the solvent and subsequent cooling of the solution gives a crystalline material melting at 86° to 87° C. in a yield of 57%.

This compound has the following analytical characteristics:

Analysis: Calculated: C 33.15; H 5.56; N 30.93; S 8.85. Observed: C 33.02; H 5.64; N 30.53; S 8.71; C 33.13; H 5.68; N 30.49; S 8.68.

IR (cm$^{-1}$) (KBr pellet) in the region of 400–1400 cm$^{-1}$ 1265s, 1222vs, 1182m, 1151m, 1116m, 1083m, 937vs, 914m, 875s, 842m, 811m, 770s, 646s, 577m.

Mass spectrum m/e 362 (M+) 6%, 320 (M-Az)+ 100%.

$^{31}$p NMR (in solution in CDCl$_3$) $\delta^{31}$p 35.4 ppm (in relation to 85% H$_3$PO$_4$).

This preparation also leads to an end product which has a melting point of 104° C. and of which the results of elemental analysis, $^{31}$p NMR and mass spectrometry are identical with those which have just been described with reference to the sample melting at 86° to 87° C.

However, the IR data (KBr pellet, 400–1400 cm$^{-1}$ region) are slightly different:

1265s, 1226vs, 1170sh, 1153s, 1084s, 942s br, 912m, 882m, 867m, 813m, 766m, 711s, (646, 638)vs, 542m.

The two products thus prepared in fact correspond to two different crystallographic forms and have exactly the same activity with respect to the three tumours described below.

EXAMPLE 3

Preparation of the compound NPAz$_2$)$_2$NSOPh

A solution of 144.0 mMoles of freshly distilled aziridine in 40 ml of dry diethylether is added dropwise over a period of 1 hour to a solution of 9.0 mMoles of (NPCl$_2$)$_2$NOSPh in 40 ml of dry diethylether cooled to a temperature of $-75°$ C. (mixture of acetone and liquid nitrogen) under vigorous stirring. The reaction mixture is left to return slowly to room temperature, followed by stirring for another 17 hours at that temperature. The solution is filtered and the residue (consisting essentially of polymeric material) is extracted three times with 30 ml of dry diethylether.

After the mother liquor and the extracts have been combined, the solvent is evaporated in vacuo. The crude reaction product is extracted with three portions of 120 ml of dry diethylether.

Recrystallisation by partial evaporation of the solvent and subsequent cooling of the solution gives a crystalline material melting at 108°–109° C. in a yield of 50%.

This compound has the following analytical characteristics:

Analysis: Calculated: C 42.43; H 5.33; N 24.67; S 8.07. Observed: C 42.74; H 5.34; N 24.72; S 8.19; C 42.48; H 5.45; N 24.56; S 8.16.

IR (cm$^{-1}$) in the region 400–1400 cm$^{-1}$ (nujol) 1267s, 1247vs, 1210vs br, 1150vs, 1085s, 939vs br, 878m, 842m, 777m, (711, 102)s, 648s, 579s, 534m.

Mass spectrum m/e 397 (M+) 100%. $^{31}$p NMR (in solution in CDCl$_3$) $\delta^{31}$p 34.1 ppm (in relation to 85% H$_3$PO$_4$).

EXAMPLE 4

Preparation of the compound (NPAz$_2$)$_2$NSO piperidino

A solution of 80.0 mMoles of freshly distilled aziridine in 40 ml of dry ether is added to a solution of 10.0 mMoles of (NPCl$_2$)$_2$NSOCl in 40 ml of dry diethylether cooled to $-75°$ C. The reaction mixture is filtered at −20° C. The remaining solution is allowed to react with 20 mMoles of piperidine in ethereal solution at −20° C.

The (NPAz$_2$)$_2$NSO piperidino is obtained and identified by mass spectrum.

Using the process of example 4 and instead of piperidine:

morpholine, the (NPAz$_2$)$_2$NSO morpholino
butanol, the (NPAz$_2$)$_2$NSO butoxy
phenol, the (NPAz$_2$)$_2$NSO phenoxy, may be obtained.

The starting compound used in the preceding Examples may be prepared as described in the following publications or even by similar processes:

(NPCl$_2$)$_2$NSOF—H. H. Baalmann and J. C. van de Grampel, Rec. Trav. Chim. (Pays-Bas) 92, 1237-1239 (1973), (NPCl$_2$)$_2$NSOCl—H. H. Baalmann, H. P. Velvis, J. C. van de Grampel, Rec. Trav. Chim. (Pays-Bas), 91, 935-941 (1972), (NPCl$_2$)$_2$NSOPh—J. B. van den Berg, B. de Ruiter, J. C. van de Grampel, Z. Naturforsch., 31b, 1216-1218 (1976).

The compounds (NPAz$_2$)$_2$NSOF, (NPAz$_2$)$_2$NSOAz and (NPAz$_2$)$_2$NSOPh were tested for their pharmacological activity.

It was found first of all that the solubility of the three compounds of Examples 1 to 3 is equal to or greater than 20 g/liter which is thus largely sufficient for the preparation of injectable formulations in aqueous solution.

The toxicity of these compounds was determined in Swiss or DBA/2 mice.

The mortality which occurred systematically 5 and 6 days after administration was recorded in dependence upon the dose injected and enabled the lethal dose 0 corresponding to the maximum non-lethal dose to be deduced therefrom. The results are not affected by the species of mice used. It was found that:

the lethal dose 0 of the compound (NPAz$_2$)$_2$NSOF is 50 mg/kg,
the lethal dose 0 of the compound (NPAz$_2$)$_2$NSOAz is 210 mg/kg,
the lethal dose 0 of the compound (NPAz$_2$)$_2$NSOPh is 250 mg/kg.

Hereinafter are given some examples of pharmaceutical preparations for the compounds of the invention.

PREPARATION EXAMPLE 1

| Compound of example 2, | 50 mg |
|---|---|
| Physiological saline solution, | q.s.p. 10 ml |

The compound is dissolve in the saline solution and the obtained solution is put in ampul.

PREPARATION EXAMPLE 2

Composition for 1 capsule:

| Compound of example 2, | 200 mg |
|---|---|
| lactose, | 50 mg |
| Patato starch, | 50 mg |
| Crystal cellulose, | 109 mg |
| Magnesium stearate, | 1 mg |

PREPARATION EXAMPLE 3

Composition for 1000 mg of granule:
The following ingredients are granulated by known methods:

| Compound of example 3, | 100 mg |
|---|---|
| Lactose, | 550 mg |
| Corn starch, | 330 mg |
| Hydroxypropyl cellulose, | 20 mg |

PREPARATION EXAMPLE 4

Composition for suppositories of 1 g:

| Compound of example 2, | 500 mg |
|---|---|
| Witepsol W-35 (made by Dynamite Nobel Co.) | 500 mg |

PREPARATION EXAMPLE 5

Composition in ointment from is prepared by mixing the following engredients:

| Compound of example 1, | 2,0 g |
|---|---|
| White vaseline, | 23,0 g |
| Propylene alcohol, | 12,0 g |
| Sodium laurylsulfate, | 1,5 g |
| Ethyl p-hydroxybenzoate, | 0,025 g |
| Propyl p-hydroxybenzoate, | 0,015 g |
| Purified water, | q.s.p. 100 g |

ANTITUMORAL ACTIVITY

The antitumoral activity tests were carried out on DBA/2 mice for leukaemia P 388 and leukaemia L 1210 and on Black C 57 mice for melanoma B 16.

These tests were conducted either by single injection in different doses on day D+1 depending on the graft of the tumour or by multiple injections. (D is the day of the graft of the toumour.

The results observed are set out in Table I below.

In this Table:

$$\text{ILS } (\%) = \frac{T - C}{C} \times 100$$

T (in days) being the mean period of survival of the mice treated in days,
C (in days) being the mean period of survival of the control mice.
QnD, signifies 1 injection every n days from day D + 1,
thus, "3 injections Q4D" signifies  1 injection on D + 1
1 injection on D + 5
1 injection on D + 9

SOF = compound (NPAz$_2$)$_2$NSOF
SOAz = compound (NPAz$_2$)$_2$NSOAz
SOPh = compound (NPAz$_2$)$_2$NSOPh

| TUMOUR | PROTOCOLL (i.p. route) COMPOUND | DOSE (mg/kg/d) | ILS (%) |
|---|---|---|---|
| L 1210 | 1 injection D + 1 SOF | 25 | 27 |
|  |  | 40 | 40 |
|  |  | 50 | 48 |
|  | 3 injections Q3D | 25 | 24 |
|  | 1 injection D + 1 | 10 | 20 |
|  |  | 25 | 44 |
| P 388 | SOF | 50 | 98 |
|  | 3 injections Q4D | 10 | 51 |
|  |  | 25 | 118 |
|  | 1 injection D + 1 | 100 | 28 |
|  |  | 150 | 48 |

| | -continued | | |
|---|---|---|---|
| L 1210 | SOAz | | |
| | 3 injections Q3D | 50 | 22 |
| | | 100 | 46 |
| | 1 injection D + 1 | 50 | 35 |
| | | 100 | 73 |
| | | 150 | 134 |
| | | 175 | 188 |
| P 388 | SOAz | 200 | 4/10 cures |
| | 3 injections Q4D | 50 | 73 |
| | | 100 | 196 |
| | 2 injections Q4D | 150 | 2/10 cures |
| | 1 injection D + 1 | 50 | 33 |
| | | 100 | 47 |
| B 16 | SOAz | 150 | 64 |
| P 388 | 1 injection D + 1 SOPh | 200 | 113 |

It can be seen that the main results of this Table are as follows:

The compound (NPAz$_2$)$_2$NSOAz exhibits substantial anti-tumoral activity with a single injection against leukemia which is rare not to say exceptional for non-metallic anti-cancer drugs.

The fact that the ILS (196%) obtained with a triple injection Q4D of 3×100 mg/kg is substantially three times that (73%) obtained with a single injection of 100 mg/kg on day D+1 prompts the assumption that this compound is active not only on early leukaemia P 388 but also on advanced leukaemia P 388.

In addition, the accompanying FIGURE demonstrates a seemingly unique phenomenon in the chemical treatment of cancer, i.e. with a single injection, the ILS of the compound/P388 system increases exponentially with the injected dose, tending towards the equation line x=200 mg/kg.

We claim:

1. Compounds corresponding to the following formula:

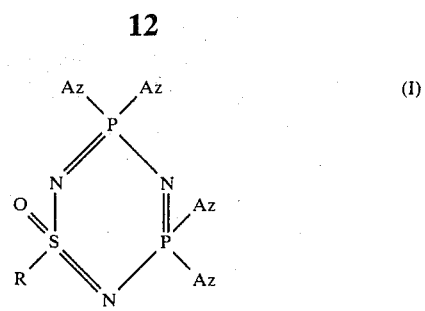

in which R is a radical which cannot be hydrolysed at a neutral pH and at room temperature selected from the group consisting of a halogen atom, a hydroxy radical, an amino radical, an alkyl or an alkoxy radical of 1 to 7 carbon atoms, an alkenyl or alkynyl radical of 2 to 7 carbon atoms, a monocyclic aryl or aryloxy radical, and an N-alkyl or N,N-dialkyl amino radical, and Az is an unsubstituted 1-aziridinyl radical or a 1-aziridinyl radical substituted with an alkyl or an alkoxy radical of 1 to 7 carbon atoms.

2. Compounds as claimed in claim 1, characterised in that the radical Az is the 1-aziridinyl radical

3. Compounds as claimed in claim 1 or 2, characterised in that R is a fluorine atom.

4. Compounds as claimed in any of claims 1 or 2, characterised in that R is a fluorine, chlorine, bromine, iodine atom, a trifluoromethyl, phenyl, dimethylamino, monomethylamino, aziridino radical.

5. Compounds as claimed in claim 1 or 2, characterised in that R is the phenyl radical.

6. Compounds as claimed in claim 1 or 2, characterised in that R is the aziridinyl radical.

* * * * *